(12) United States Patent
Cankar et al.

(10) Patent No.: US 11,007,090 B2
(45) Date of Patent: May 18, 2021

(54) METHOD OF WINDING UP TAMPON MATERIAL

(71) Applicant: Johnson & Johnson GmbH, Neuss (DE)

(72) Inventors: Thomas Cankar, Wuppertal (DE);
Markus Klar, Wuppertal (DE);
Markus Anger, Wuppertal (DE);
Martin Bergermann, Wuppertal (DE);
Jens-Petter Arnesen, Sezanne (FR)

(73) Assignee: Johnson & Johnson GmbH, Neuss (DE)

( * ) Notice: Subject to any disclaimer, the term of this patent is extended or adjusted under 35 U.S.C. 154(b) by 166 days.

(21) Appl. No.: 16/066,026

(22) PCT Filed: Dec. 30, 2016

(86) PCT No.: PCT/IB2016/058120
§ 371 (c)(1),
(2) Date: Jun. 25, 2018

(87) PCT Pub. No.: WO2017/115337
PCT Pub. Date: Jul. 6, 2017

(65) Prior Publication Data
US 2019/0015263 A1    Jan. 17, 2019

Related U.S. Application Data

(60) Provisional application No. 62/273,791, filed on Dec. 31, 2015.

(51) Int. Cl.
*A61F 13/20*        (2006.01)
*B65H 69/04*        (2006.01)
(Continued)

(52) U.S. Cl.
CPC ...... *A61F 13/2085* (2013.01); *A61F 13/2082* (2013.01); *B65H 57/20* (2013.01);
(Continued)

(58) Field of Classification Search
CPC .. A61F 13/20; A61F 13/2094; A61F 13/2082; A61F 13/34; A61F 13/2085; A61F 13/2088; B65H 67/056; B65H 67/04
(Continued)

(56) References Cited

U.S. PATENT DOCUMENTS 2,566,190 A  *  8/1951  Greiner .............. A61F 13/2051
                                                            28/118
2,706,986 A      4/1955  Carrier
(Continued)

FOREIGN PATENT DOCUMENTS

DE       616691 C       8/1935
EP      2298259 A       3/2011
(Continued)

OTHER PUBLICATIONS

International search report and written opinion for PCT/IB2016/058120 dated Mar. 10, 2017.
(Continued)

*Primary Examiner* — Jillian K Pierorazio

(57) ABSTRACT

An improved apparatus for forming tampon blanks for further processing into compressed, self-sustaining tampons, permits increased speed and accuracy of the process step. The apparatus includes a sliver guide; a gripper capable of reciprocating motion and arranged and configured to cooperate with the sliver 5 guide to grasp an end of a sliver maintained therein; a winding mandrel; a plurality of winding cups; and e) a string application and knotter apparatus comprising a circular ring bearing having a string conveyor mounted thereon. The circular ring bearing of the string
(Continued)

application and knotter apparatus defines a plane perpendicular to the sliver guide and motion of the gripper and parallel to the 10 winding axis of the winding mandrel.

2 Claims, 4 Drawing Sheets

(51) Int. Cl.
  *B65H 57/20* (2006.01)
  *A61F 13/34* (2006.01)
(52) U.S. Cl.
  CPC .............. *B65H 69/04* (2013.01); *A61F 13/34* (2013.01); *B65H 2701/31* (2013.01)
(58) Field of Classification Search
  USPC ........................... 28/118, 120; 19/149; 289/2
  See application file for complete search history.

(56) References Cited

U.S. PATENT DOCUMENTS

| | | | | |
|---|---|---|---|---|
| 2,763,899 A * | 9/1956 | Hahn | ................. | A61F 13/2085 28/120 |
| 2,873,133 A * | 2/1959 | Wieser | ................ | A61F 13/2085 289/5 |
| 2,977,644 A * | 4/1961 | Wieser | ................ | A61F 13/2085 19/149 |
| 3,131,435 A * | 5/1964 | Cloots | ................ | A61F 13/2085 28/119 |
| 3,247,781 A | 4/1966 | Meckler | | |
| 3,348,866 A | 10/1967 | Etz | | |
| 3,477,102 A | 11/1969 | Etz | | |
| 3,688,346 A * | 9/1972 | Johst | ................ | A61F 13/2085 28/120 |
| 3,814,469 A * | 6/1974 | Simon | ................ | A61F 13/2085 289/1.5 |
| 3,818,912 A * | 6/1974 | Etz | ..................... | A61F 13/2085 604/358 |
| 3,852,847 A * | 12/1974 | Etz | ..................... | A61F 13/2085 28/120 |
| 3,946,463 A * | 3/1976 | Warncke | ............. | A61F 13/2085 28/120 |
| 4,012,809 A * | 3/1977 | Warncke | ............. | A61F 13/2085 28/120 |
| 4,019,226 A * | 4/1977 | Yamauchi | ........... | A61F 13/2085 28/120 |
| 4,067,087 A * | 1/1978 | Mast, Jr. | ............. | A61F 13/2085 28/118 |
| 4,177,544 A * | 12/1979 | Bischkopf | ........... | A61F 13/2085 28/119 |
| 4,177,842 A | 12/1979 | Dilley | | |
| 4,490,894 A * | 1/1985 | Friese | ................. | A61F 13/2085 28/120 |
| 4,502,905 A * | 3/1985 | Jung | ..................... | B65B 13/327 100/27 |
| 4,816,100 A * | 3/1989 | Friese | ................... | A61F 13/206 156/191 |
| 4,836,587 A | 6/1989 | Hinzmann | | |
| 5,084,038 A * | 1/1992 | Sheldon | .............. | A61F 13/2082 156/193 |
| 5,909,884 A | 6/1999 | Schwankhart | | |
| 6,585,300 B1 * | 7/2003 | Rajala | ................ | A61F 13/2082 289/18.1 |
| 8,414,035 B2 | 4/2013 | Bell | | |
| 8,622,440 B2 | 1/2014 | Crichton et al. | | |
| 2002/0060455 A1* | 5/2002 | Thomas | ............... | B65H 65/005 289/2 |
| 2012/0326442 A1* | 12/2012 | Crichton | ................ | B65B 13/26 289/2 |
| 2013/0036584 A1* | 2/2013 | Ishikawa | ............. | A61F 13/2085 28/118 |
| 2013/0067707 A1* | 3/2013 | Kaiser | ................ | A61F 13/2094 28/118 |
| 2015/0000490 A1 | 1/2015 | Durling et al. | | |

FOREIGN PATENT DOCUMENTS

| | | |
|---|---|---|
| GB | 742546 A | 12/1955 |
| JP | S57069857 A | 4/1982 |
| SU | 149303 | 8/1962 |
| SU | 247460 A | 7/1969 |
| WO | WO 1999/027878 A | 6/1999 |
| WO | WO 2001/002144 A | 1/2001 |
| WO | WO 2001/043680 A | 6/2001 |
| WO | WO 2011/086054 A | 7/2011 |

OTHER PUBLICATIONS

Search report dated Mar. 26, 2020, for RU application 2018127836.

* cited by examiner

METHOD OF WINDING UP TAMPON MATERIAL

CROSS-REFERENCE TO RELATED APPLICATIONS

This application is the national stage filing under USC 371 of international application PCT/IB2016/058120 filed on Dec. 30, 2016, which claims the benefit of U.S. provisional application 62/273,791 filed on Dec. 31, 2015.

FIELD OF THE INVENTION

The present invention relates to a method of winding up tampon material in a tampon manufacturing process.

BACKGROUND OF THE INVENTION

Methods of forming tampons are known.
In view of the shortcomings of the prior art, what is needed is a more efficient process of winding up tampon material for improved tampons.

SUMMARY OF THE INVENTION

The present invention relates to high-speed methods for manufacturing tampon blanks for further processing into compressed, self-sustaining tampons.

The present invention also relates to apparatus to practice such methods.

DETAILED DESCRIPTION OF THE INVENTION

This invention relates to a method and machine for applying a withdrawal string to a tampon for feminine hygiene. In the present method, the string is placed about a web that is in turn, rolled up to form a cylindrical tampon blank.

String Application and Knotter Apparatus

Figure 1:
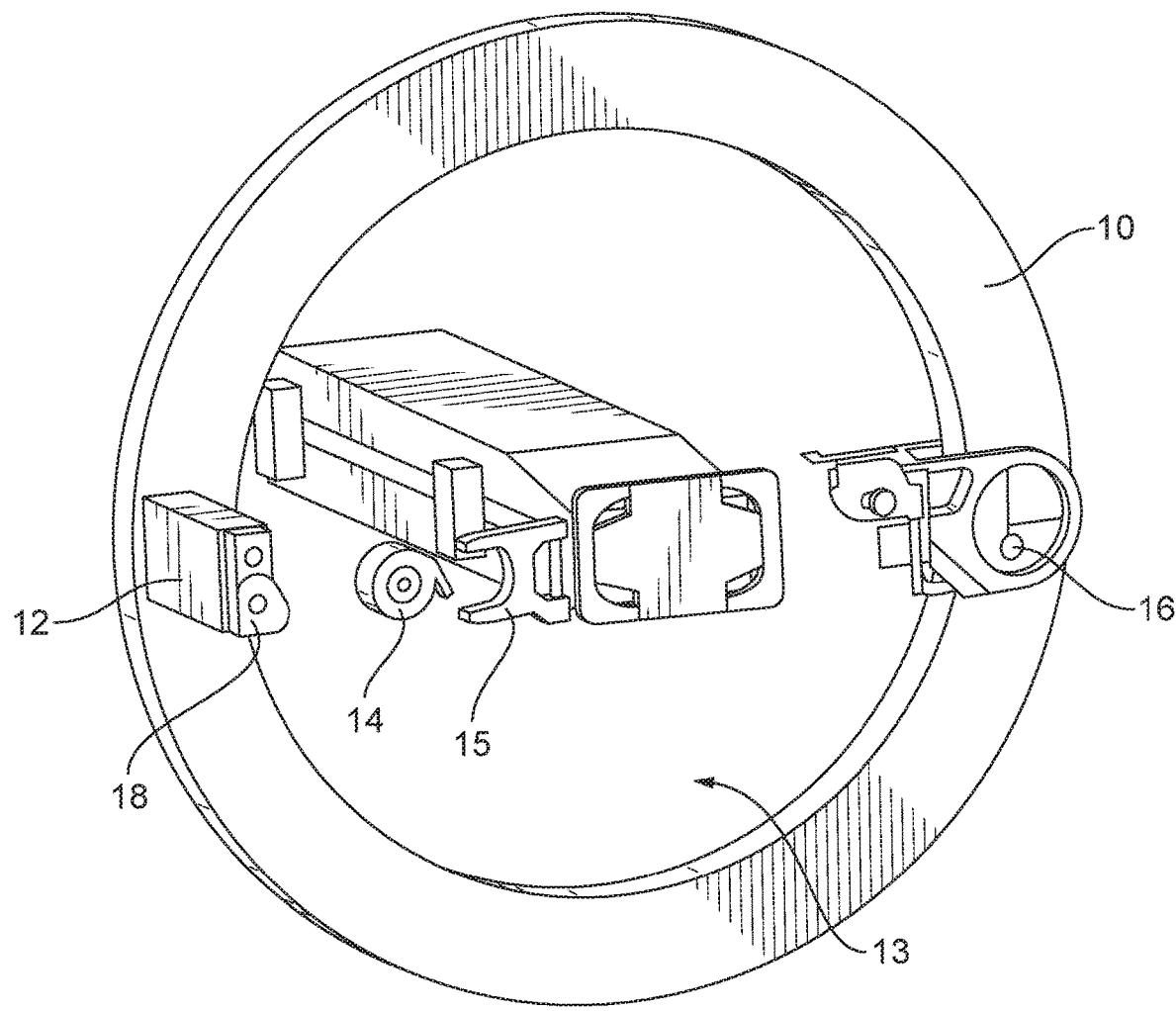
FIG. 1 is a schematic view of the string application and knotter apparatus according to one embodiment of the invention.
Figure 2:
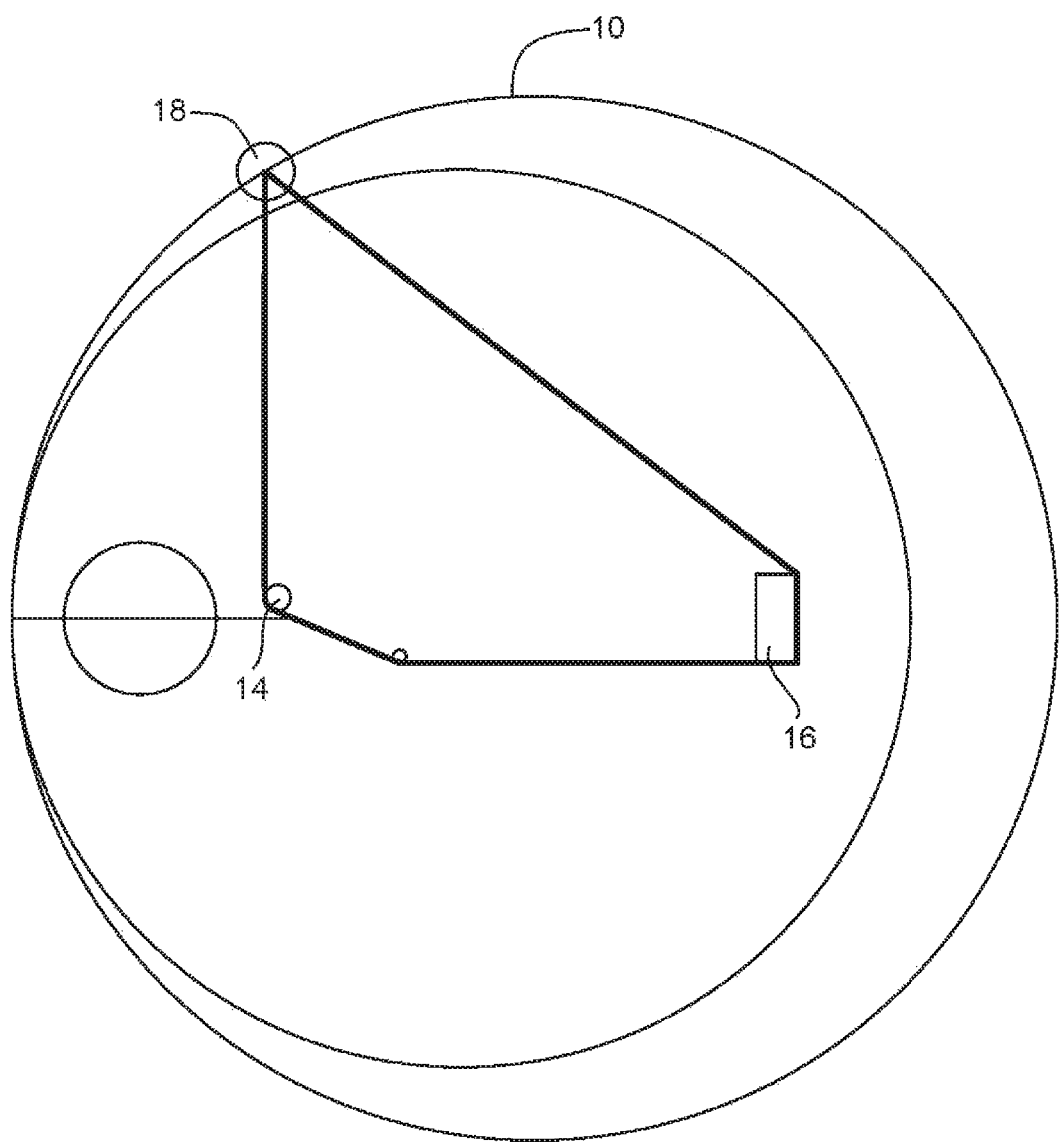
FIG. 2 is a diagram of elements of the string application and knotter apparatus that determine the string length.

A string application and knotter apparatus 1 is defined by an outer circular string path. As shown in FIG. 1, the circular string path is defined by a circular ring bearing 10 having a string conveyor 12 mounted thereon. The interior 13 of the apparatus is substantially open to permit passage of the tampon sliver and transport elements of the system. In addition to the outer circular string path 10 and string conveyor 12, the string application and knotter apparatus includes a snake 14, a hook 16, and a knife. The length of the string and the location of the knot with respect to the end of the string loop formed by the string application and knotter apparatus is determined by the geometry of the following elements: the hook, the snake, and the knife as shown in FIG. 2.

The string conveyor 12 includes a clamp 18 to hold the leading end of the string as the string conveyor travels around the circular string path. One revolution of the string conveyor completes one cycle of the string application and knotter apparatus. The string conveyor begins at an initial angular location with respect to the top of the ring bearing.

During the cycle of the string application and knotter apparatus, the string is transported and processed. The ring bearing 10 has a variable rotation speed as it completes its revolution. A single revolution of the string conveyor 12 constitutes a single string delivery, including accurate control of string length and knotting of the string at a desired location. The knot is made as both string ends, trapped by a spring-loaded ball, slide over the hook shoulder together and get caught by the knot control lever that tightens the knot.

Unlike earlier string application and knotter apparatus that use a chain-drive system, such as described in Etz, U.S. Pat. No. 3,348,866, and Simon, U.S. Pat. No. 3,814,469, the substantially rigid ring bearing provides greatly improved control of the location of the string conveyor. Thus, rapid angular acceleration (and/or deceleration) is not affected by movement between chain links. Such movement can increase as the links wear against each other. This allows the string conveyor motion around the apparatus to accelerate during simple movements, and to decelerate for more precise control during complex manipulations of the string and/or engagement with other process elements. For example, the string conveyor 12 can move rapidly about the apparatus to draw out the pre-determined string length, and it can slow for knot tying and engagement with the winding mandrel.

Tampon Blank Winder

Figure 3:
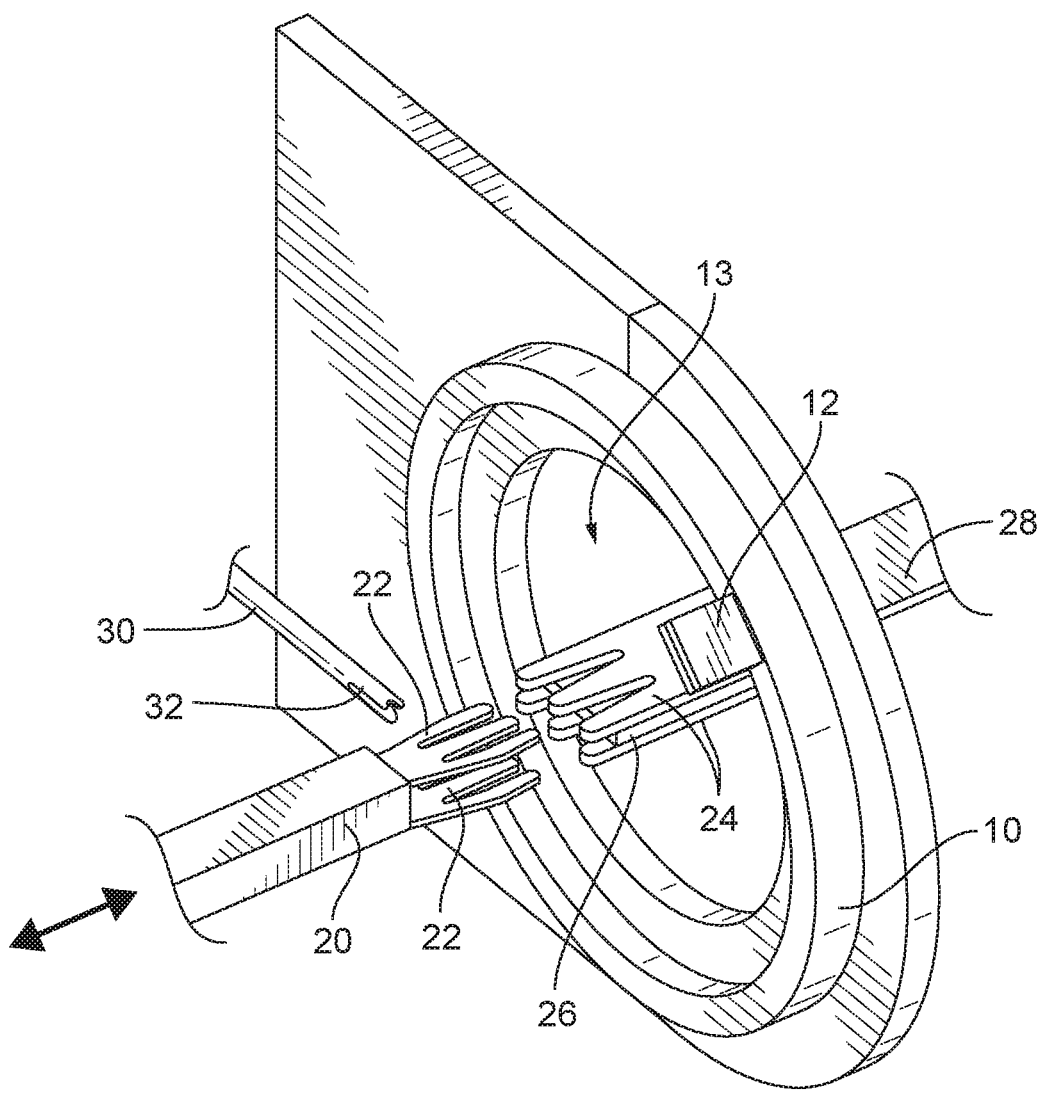
FIG. 3 is a perspective view of elements of the tampon blank winder according to one embodiment of the present invention.
Figure 4:
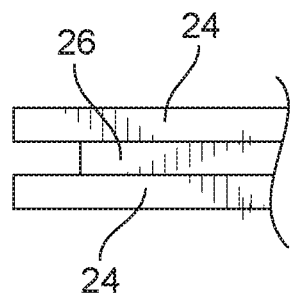
FIG. 4 is an enlarged side elevation of the sliver guide of FIG. 3.

The tampon blank winder includes a gripper mechanism to draw the absorbent sliver into the winder, and a winding mandrel. As shown in FIGS. 3 and 4, the gripper 20 includes a pair of multiple-tined clamps 22. The gripper is driven to advance into and withdraw from a sliver guide 24. The gripper clamps 22 are in an open position as they enter the sliver guide and closed on the leading end 26 of the sliver 28 to pull it through the string application and knotter apparatus (represented in FIG. 3 by ring bearing 10 and string conveyor 12—other elements of the string application and knotter apparatus being removed for clarity) and into the sliver winding station. In addition to the back and forth motion into and out of the sliver guide, the gripper may also change elevation during this motion.

In a preferred embodiment, the sliver guide comprises a tapered or narrowed end section to control the location of the leading end of the sliver as it is delivered to the tampon blank winder.

The gripper can be servodriven and can be controlled with an adaptive profile. A sensor detects the leading end of the sliver in the conveyer belt and into the sliver guide. The gripper that is advancing into the sliver guide will adapt its speed to gripe the sliver in the same location.

Alternatively, the gripper could be equipped with a single drive on a crankshaft. In this configuration the gripper clamp opening is actioned by a small lever. As the gripper travels forward it closes and reopens in the front position as the lever pull it open. When driving back it will close and grip the sliver before being pulled open again in the back position. This operating mode is improved by use of an "intelligent" gripper control.

As shown in FIG. 3, the winding apparatus includes a slotted winding mandrel 30 that has an elongate slot 32 having a slot opening sufficient to accommodate the thickness of the sliver 28 and a slot depth sufficient to accommodate the width of the sliver 28. The leading end of the slotted winding mandrel has a string guide to center the string across the slot opening (such as shown in Johst et al., U.S. Pat. No. 3,688,346, and Etz, U.S. Pat. No. 3,852,847, the disclosures of which is herein incorporated by reference). The slotted winding mandrel is arranged and configured to rotate to wind up a desired length of sliver to form a tampon blank. The winding apparatus may also include a top former to hold the sliver 28 against the winding mandrel 30 as the sliver is wound by the slotted winding mandrel 30.

Figure 5:
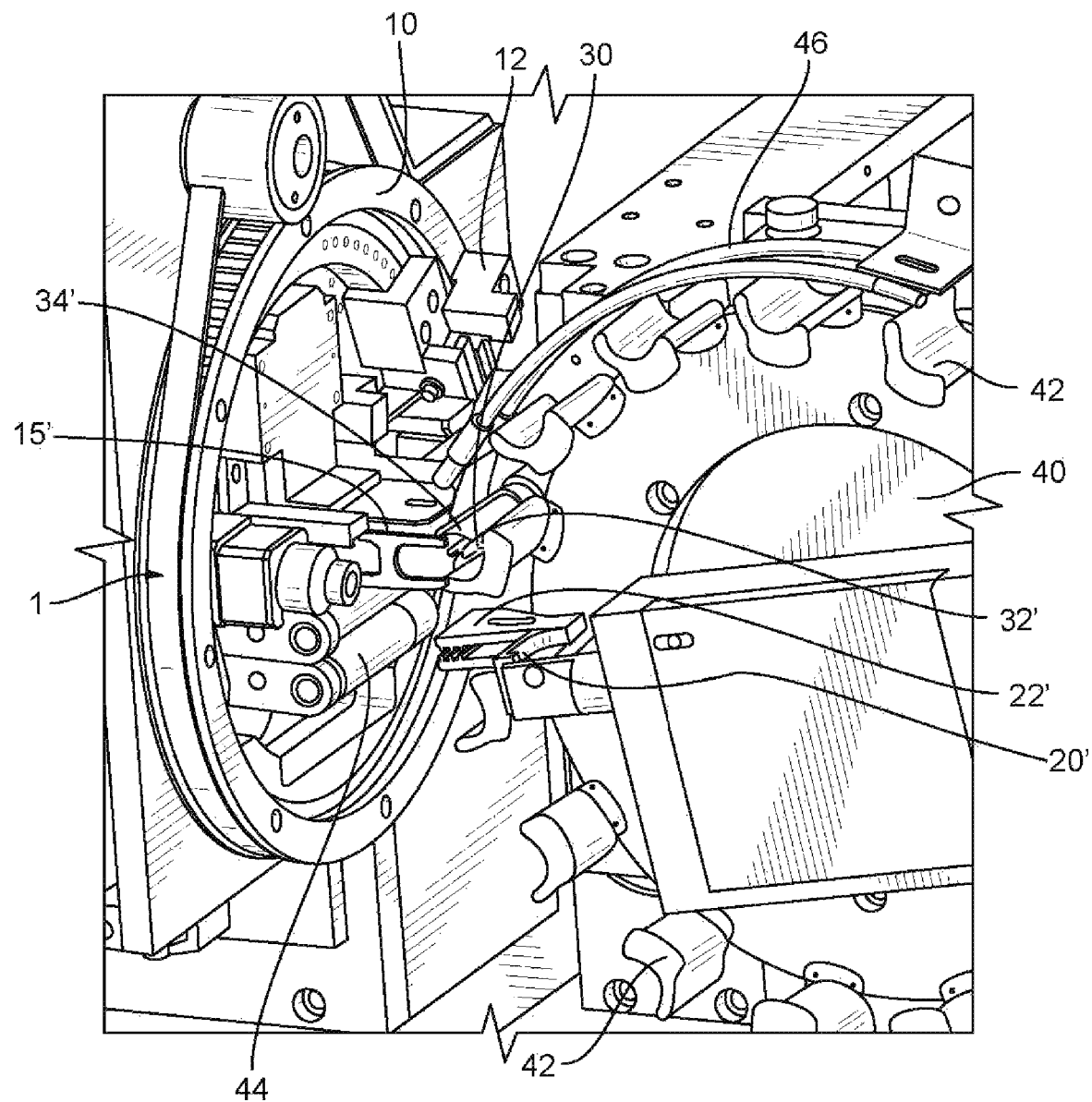
FIG. 5 is a perspective view of a string application and knotter apparatus and tampon blank winder according to another embodiment of the present invention.

In an alternative embodiment, shown in FIG. 5, the winding apparatus may interact with a turntable 40 to index the tampon-forming materials as they are processed from tampon sliver to tampon blank. The turntable 40 includes a plurality of carriers 42 in the form of a half hollow cylinder pivotally mounted thereon. The turntable is mounted on an axis perpendicular to the direction of travel of the gripper. As shown in FIG. 5, the clamps 22' of gripper 20' do not require the tines of the gripper of the previous embodiment. This is permitted by the use of a conveyor 44 that delivers the sliver end (not shown) to the winding apparatus.

In operation, the string conveyor 12 clamps the end of the string supply and begins the circular cycle of movement. The ring bearing 10 and string conveyor 12 revolve in a counter clockwise motion to pull the string from the string supply and pass it around the snake 14', hook 16', and back to the cutting location where the string conveyor also clamps the new end of the string supply. The string conveyor 12 also delivers the two ends of the looped string to the knotter. The knot is made as both string ends, trapped by a spring-loaded ball, slide over the hook shoulder together and get caught by the knot control lever that tightens the knot.

As the string is being looped around the snake 14' and the hook 16', the gripper 20' advances through the interior 13 of the string application and knotter apparatus. The gripper 20' then clamps the leading end of the sliver and retracts, pulling the leading end of the sliver through the interior 13 of the string application and knotter apparatus and across a carrier 42'. This pull is supported by the intermittent clockwise rotation of the turntable 40'. As soon as the gripper 20 has passed the carrier 42' the turntable 40 starts to rotate, thereby elevating the carrier 42', and supports pulling the leading end of the sliver through the interior 13' of the string application and knotter apparatus and to place the sliver in front of the slot 32' of the slotted winding mandrel 30'. As the gripper 20' fully retracts, the slotted winding mandrel 30' extends to capture an intermediate portion of the sliver within its slot 32'. Tension on the string loop then pulls the loop holder 15 toward the string guide 34' at the leading end of the slotted winding mandrel 30' and off of the loop holder 15' and onto the string guide 34'. In a preferred embodiment, shown in FIG. 5, the winding mandrel 30' is spaced from the path of the string on the gripper side of the string application and knotter apparatus 1. The winding mandrel 30' rotates as the gripper 20' releases the leading end of the sliver, and the rotation of the winding mandrel 30' draws the rest of the sliver upon itself. The optional top former may provide sufficient sliver control as the sliver is wound about the mandrel 30'. The rotation of the winding mandrel 30' also winds the string extending from the withdrawal end of the tampon blank about the winding mandrel 30'. The tampon blank is transferred to a carrier 42 for movement to further processing operations, including a tampon press, dome former, and primary packaging. A top guide 46 may be used to maintain the tampon blanks in their respective carriers during motion along the revolver.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. Apparatus for forming tampon blanks for further processing into compressed, self-sustaining tampons, the apparatus comprising:
    a) a sliver guide;
    b) a gripper capable of reciprocating motion and arranged and configured to cooperate with the sliver guide to grasp an end of a sliver maintained therein;
    c) a winding mandrel;
    d) a plurality of carriers; and
    e) a string application and knotter apparatus comprising a substantially rigid circular ring bearing having a string conveyor mounted thereon arranged and configured to rotate about the sliver;

wherein the circular ring bearing of the string application and knotter apparatus defines a plane perpendicular to the sliver guide and motion of the gripper and parallel to the winding axis of the winding mandrel.

2. A process for manufacturing tampon blanks for further processing into compressed, self-sustaining tampons, the process comprising the steps of:
    a) drawing a fibrous web from a fibrous web supply, through a sliver guide and across a carrier disposed on a turntable by grabbing a free end of the fibrous web supply with a gripper and drawing the gripper away from the fibrous web supply;
    b) severing the fibrous web from the fibrous web supply to form an elongate fibrous web having a first end held by the gripper and a second end, distal the first;
    c) elevating the carrier while the first end remains held by the gripper and the second end is restrained by the sliver guide wherein the carrier is disposed perpendicular to a central portion of the elongate fibrous web;
    d) advancing a winding mandrel across the central portion of the elongate fibrous web, wherein the winding mandrel has a slot arranged and configured to accept the elongate fibrous web therein;
    e) rotating the winding mandrel as the gripper releases the first end of the elongate fibrous web to form a tampon blank; and
    f) transferring the tampon blank to the carrier.

* * * * *